United States Patent [19]

Rose et al.

[11] 4,129,414

[45] Dec. 12, 1978

[54] OXIDATION HAIR COLORANTS CONTAINING WATER-SOLUBLE POLYHALOGEN 3-AMINOPHENOLS AS COUPLERS

[75] Inventors: David Rose, Hilden; Ferdi Saygin, Erkrath; Edgar Lieske, Dusseldorf, all of Germany

[73] Assignee: Henkel Kommanditgesellschaft auf Aktien (Henkel KGaA), Dusseldorf-Holthausen, Germany

[21] Appl. No.: 661,548

[22] Filed: Feb. 26, 1976

[30] Foreign Application Priority Data

Mar. 3, 1975 [DE] Fed. Rep. of Germany ....... 2509096

[51] Int. Cl.² ............................................... A61K 7/13
[52] U.S. Cl. ........................................ 8/10.2; 8/10.1; 8/11; 8/32; 260/575
[58] Field of Search ...................... 260/575; 8/10.2, 11, 8/32

[56] References Cited

U.S. PATENT DOCUMENTS

| | | | |
|---|---|---|---|
| 3,128,232 | 4/1964 | Wilmsmann et al. | 8/10.2 |
| 3,200,040 | 8/1965 | Lange | 8/10.2 |
| 3,415,608 | 12/1968 | Tucker | 8/10.2 |
| 3,558,259 | 1/1971 | Kalopissis et al. | 8/10.2 |
| 3,738,799 | 6/1973 | Kalopissis et al. | 8/10.2 |
| 3,879,464 | 4/1975 | Kalopissis et al. | 8/10.2 |
| 3,948,596 | 4/1975 | Kalopissis et al. | 8/10.2 |

FOREIGN PATENT DOCUMENTS

| | | | |
|---|---|---|---|
| 103505 | 6/1898 | Fed. Rep. of Germany | 8/10.2 |
| 1492167 | 9/1972 | Fed. Rep. of Germany | 8/10.2 |

*Primary Examiner*—Albert T. Meyers
*Assistant Examiner*—Vera C. Clarke
*Attorney, Agent, or Firm*—Hammond & Littell

[57] ABSTRACT

Oxidizable developer-coupler combinations wherein the coupler is a water-soluble polyhalogen 3-aminophenol are stable in the absence of free oxygen and chemical oxidizing agents. They provide hair dyeings of specially desirable shades. The dyeings are color fast, wash-fast, thermostable, and non-toxic. The combinations can be applied in customary vehicles. Their dyeing properties are developed by air oxidation, by peroxides, or by both at an acid, neutral or alkaline pH.

21 Claims, No Drawings

OXIDATION HAIR COLORANTS CONTAINING WATER-SOLUBLE POLYHALOGEN 3-AMINOPHENOLS AS COUPLERS

FIELD OF THE INVENTION

The invention relates to compositions of the oxidizable developer-coupler type useful for the dyeing of hair. The invention includes the developer-coupler combinations, aqueous systems for application of the compositions to hair, the processes involved, and a specific novel coupler.

PRIOR ART

Oxidation colors are formed by oxidative coupling (i.e., by reaction) of a developer component with a coupling component under oxidizing conditions. They are preferred as hair dyes because they provide intensely colored dyeings of good fastness. The developers have generally been nitrogen bases like p-phenylenediamine, diaminopyridine, 4-amino-pyrazolone and their derivatives, as well as the heterocyclic hydrazones. The couplers which have been used in the past have been usually m-phenylenediamine, phenol, naphthol, resorcinol, pyrazolone, and their derivatives.

OBJECTS OF THE INVENTION

Good oxidation developer-coupler combinations must meet the following primary requirements before they can be regarded as suitable latent hair dyeing materials.

On oxidation, they must form a desirable color nuance of sufficient intensity to meet commercial standards. They must have a sufficient to very good absorption power on human hair (i.e., they should be self-substantive to hair), and they should be toxicologically and dermatologically harmless. Furthermore, it is of importance that they produce vigorous color tones which correspond as far as possible to natural hair color nuances. Furthermore, the stability of the dyeings effected (their light-fastness, wash-fastness and thermostability) are of great importance in order to avoid shifts from the original color nuance, or even changes to other color tones.

The problem in searching for usable developer-coupler combinations which act as hair dyes when oxidized (hereinafter termed "oxidation hair dyes") was therefore to find suitable water-soluble components which meet the above-mentioned requirements in optimal manner.

It is therefore a further object of the invention to provide the art with developer-coupler combinations which will meet the above requirements and provide oxidative hair dyeing compositions which will develop their tinctorial properties rapidly, by the action of the air or a mild, harmless oxidizing agent, to provide satisfactory dyeings.

THE INVENTION

The discovery has now been made that the above objects are attained in very satisfactory manner when the coupler component in oxidizable developer-coupler hair dye compositions is a polyhalogen 3-aminophenol of the formula:

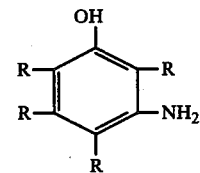

wherein two to three of the R's represent halogen (fluoro, chloro and/or bromo) and the remaining R or R's represent hydrogen. These polyhalogen 3-aminophenols are useful for the above-stated purposes, both in their free base form and in the form of their water-soluble salts.

Thus the R's which represent halogen may be selected from the group consisting of fluoro, chloro and bromo.

The developer-coupler combinations of the present invention, when applied to hair and oxidized thereon, provide a spectrum of very intensive color nuances which are not achieved by presently-known developer-coupler combinations. This discovery, therefore, represents an essential enrichment of the possibilities of dyeing hair by use of oxidizable developer-coupler combinations. Beyond that, the polyhalogen-substituted m-aminophenols according to the invention are characterized by good solubility in water, good storability, and toxicological as well as dermatological harmlessness.

The polyhalogen-substituted m-aminophenols to be used according to the invention as coupler components can be used either as such or in the form of their salts with inorganic or organic acids, like chlorides, sulfates, phosphates, acetates, propionates, lactates, and citrates.

Compounds suitable for use as coupler components according to the invention are, for example:

2,4-dichloro-3-aminophenol, 2,5-dichloro-3-aminophenol, 2-6-dichloro-3-aminophenol, 4,6-dichloro-3-aminophenol, 5,6-dichloro-3-aminophenol,2,4,6-trichloro-3-aminophenol, 4,5,6-trichloro-3-aminophenol, 2,5,6-trichloro-3-aminophenol, 2,4-dibromo-3-aminophenol, 2,5-dibromo-3-aminophenol, 2,6-dibromo-3-aminophenol, 4,6-dibromo-3-aminophenol, 5,6-dibromo-3-aminophenol, 2,4,6-tribromo-3-aminophenol, 4,5,6-tribromo-3-aminophenol, 2,5,6-tribromo-3-aminophenol, 2,4-difluoro-3-aminophenol, 2,5-difluoro-3-aminophenol, 2,6-difluoro-3-aminophenol, 4,6-difluoro-3-aminophenol, 5,6-difluoro-3-aminophenol, 2,4,6-trifluoro-3-aminophenol, 4,5,6-trifluoro-3-aminophenol, 2,5,6-trifluoro-3-aminophenol, 2-bromo-4-chloro-3-aminophenol, 4,6-difluoro-2-chloro-3-aminophenol.

The polyhalogen-substituted m-aminophenols to be used according to the invention as coupler components represent (with the exception of the 2,4-dihalogen-3-aminophenols, whose preparation is described below) compounds which are known in the literature. Thus, W. A. Jacobs, M. Heidelberger and J. P. Wolf describe in J. Amer. Chem. Soc. 41 (1919) p. 461 the preparation of 4,6-dichloro-3-aminophenol. The preparation of 2,4,6-trichloro-3-aminophenol by reduction of the corresponding trichloronitrophenol with tin and hydrochloric acid is described by G. Daccomo in Ber. 18 (1885) p. 1166/67.

Among polyhalogen-substituted m-aminophenols to be used as coupler components, the chlorine-substituted compounds represent the preferred compounds, and among these 2,4-dichloro-3-aminophenol has the greatest importance.

As examples for the developer components to be used in the hair coloring compositions of the invention are the primary aromatic amines which have an additional functional group in the para-position, for example, p-phenylenediamine, p-toluenediamine, p(dimethylamino)aniline, p-aminophenol, p-diaminoanisole and other compounds of the above-mentioned type, which can contain one or more additional functional groups like —OH groups, —NH$_2$ groups, —NHR groups, and —NR$_2$ groups, where R represents a $C_{1-4}$ alkyl or hydroxyalkyl radical; also diaminopyridine derivatives, heterocyclic hydrazone derivatives, and 4-aminopyrazolone derivatives like 4-amino-1-phenyl-3-carbamoylpyrazolone-5.

Of particular importance is the combination of the monohalogen-substituted m-aminophenols as coupler component with tetraaminopyrimidines of the general formula

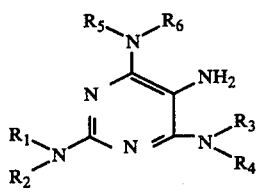

as developer component, in which $R_1$-$R_6$ denote hydrogen; a $C_{1-4}$ alkyl substituent; and —(CH$_2$)$_{1-4}$X, wherein X represents —OH, a halogen atom, —NH$_2$, —NHR' and —NR'R", wherein R' and R" denote $C_{1-4}$ alkyl substituents or are closed with the nitrogen atom to form a heterocyclic ring which can contain an additional nitrogen atom or oxygen atom, a heterocyclic 5- or 6-member ring, substituted, if desired, with one or two nitrogen atoms or with one nitrogen atom and one oxygen atom, as well as their organic or inorganic salts as developer substances. The —NR'R" substituent may thus represent a 5-6 member heterocyclic ring.

R' and R" together can be selected from the group consisting of tetramethylene, pentamethylene, azatetramethylene, azapentamethylene, oxatetramethylene, and oxapentamethylene.

The tetraaminopyrimidine developers can be used either as such (i.e., in free base form) or in the form of their salts with water-soluble inorganic or organic acids, for example, as chlorides, sulfates, phosphates, acetates, propionates, lactates, and citrates.

As tetraaminopyrimidines to be used in combination with the polyhalogenated m-aminophenols in the hair coloring compositions according to the invention are, for example, 2,4,5,6-tetraamino-, 4,5-diamino-2,6-bismethylamino-, 2,5-diamino-4,6-bismethylamino-, 4,5-diamino-6-butylamino-2-dimethylamino-, 2,5-diamino-4-diethylamino-6-methylamino-, 4,5-diamino-6-diethylamine-2-dimethylamino-, 4,5-diamino-2-diethylamino-6-methylamino-, 4,5-diamino-2-dimethylamino-6-ethylamino-, 4,5-diamino-2-dimethylamino-6-isopropylamino-, 4,5-diamino-2-dimethylamino-6-methylamino-, 4,5-diamino-2-dimethylamino-2-methylamino-, 4,5-diamino-2-dimethylamino-6-propylamino-, 2,4,5-triamino-6-dimethylamino-, 4,5,6-triamino-2-dimethylamino-, 2,4,5-triamino-6-methylamino-, 4,5,6-triamino-2-methylamino-, 4,5-diamino-2-dimethylamino-6-piperidino-, 4,5-diamino-6-methylamino-2-piperidino-, 2,4,5-triamino-6-piperidino-, 2,4,5-triamino-6-anilino-, 2,4,5-triamino-6-benzylamino-, 2,4,5-triamino-6-benzylideneamino-, 4,5,6-triamino-2-piperidino-, 2,4,6-trismethylamino-5-amino-, 2,4,5-triamino-6-di-n-propylamino-, 2,4,5-triamino-6-morpholino-, 2,5,6-triamino-4-dimethylamino-, 4,5,6-triamino-2-morpholino-, 2,4,5-triamino-6-β-hydroxyethylamino-, 4,5,6-triamino-2-β-amino-ethylamino-, 2,5,6-triamino-4-β-methylamino-ethylamino-, 2,5-diamino-4,6-bis-γ-diethylamino-propylamino-, 4,5-diamino-2-methylamino-6-β-hydroxy-ethylamino-, 5-amino-2,4,6-triethylamino-, and 2,4-bis-β-hydroxyethylamino-6-anilino-5-aminopyrimidine.

The aforesaid developer components are water-soluble and can be used in the form of their salts with water-soluble inorganic or organic acids, for example, chlorides, sulfates, phosphates, acetates, propionates, lactates and citrates.

Methods for preparation of tetraaminopyrimidines suitable for use as developers are known in the literature and can be read in the monograph by D. J. Brown, "The Pyrimidines", in the series Heterocyclic Compounds, Interscience Publishers (1962), Vols. I and II.

For the synthesis of the compounds to be used as developer components, one can start from 2,4,6-triaminopyrimidines, into which the 5-amino group is introduced by treatment with nitrous acid and subsequent reduction. But one can also start from correspondingly substituted triamino-alkylmercapto-pyrimidines and substitute the alkylmercapto-group by amines. The latter method is particularly suitable for the introduction of amino groups (or substituted amino groups) into the 2-, 4- or 6-position of the pyrimidine ring.

When used as developer components, the tetraaminopyrimidines yield, with the coupler substances generally used for oxidation hair coloring, very intensive color tones. In addition, compositions containing the tetraaminopyrimidines according to the invention as developer components, are characterized in that they possess good solubility in water and good storage stability, are toxicologically and dermatologically harmless, and provide dyeings of very good fastness.

In order to obtain vigorous color tones corresponding as far as possible to natural hair color nuances, a superior blue color is particularly important as nuancing component. But the production of such a blue color presents difficulties when the otherwise satisfactory tetraaminopyrimidines are used as developers with previously known couplers; these difficulties are due to the lack of suitability of the previously-known coupler components.

It was found that the polyhalogen-substituted m-aminophenols to be used according to the invention as coupler components are excellently suited as special blue couplers for the tetraaminopyrimidine developer system. Of particular advantage is the fact that the thermal stability of the blue color formed is substantially better than the thermal stability of the colors produced with other couplers. Furthermore, the colors produced by the couplers of the present invention are characterized by good light-fastness.

The coupler components are generally used in the hair colorants according to the invention in substantially equimolecular (i.e., stoichiometric) amounts related to the developer substances used. Though equimolecular amounts are preferable, it is no disadvantage if the coupler component is used in an excess or deficit, because any unreacted component is removed with the rinse water.

It is not necessary for the developer component and the coupler substance each to be a single substance. Rather, the developer component can be a mixture of several developer compounds and the coupler substance a mixture of two or more of polyhalogen-substituted m-aminophenols.

Beyond that, the hair coloring compositions of the invention can contain a directly-absorbing (i.e., self-substantive) dye or dyes if required to obtain a desired color nuance.

The oxidative coupling, that is, the development of the coloration (i.e., the dyeing itself), can be effected principally, as in other oxidation hair dyes, by atmospheric oxygen. Preferably, however, chemical oxidants are used for the purpose. These are particularly hydrogen peroxide (or its addition products with urea, melamine, and sodium borate), as well as mixtures of these hydrogen peroxide addition products with potassium peroxide disulfate.

As a developer component, the tetraaminopyrimidines possess the advantage that they yield fully satisfactory results when coupled by atmospheric oxygen, so that hair damage by the other oxidants used in oxidative coupling is avoided. But if a simultaneous brightening effect (in addition to dyeing) is desired, oxidizing agents must be used.

The oxidizable developer-coupler compositions of the present invention are best applied in an aqueous system, preferably by incorporation into any of the cosmetic carriers or excipients used for applying treating agents to hair, such as aqueous creams, emulsions, gels, or simple solutions, with or without thickener. They may be applied without oxidizing agent, but in most instances it will generally be found convenient to add an effective amount of one of the above-mentioned oxidants immediately before the preparation is applied on the hair. The concentration of the coloring components in the aqueous carrier is 0.2% to 5% by weight, preferably 1% to 3% by weight of the preparation. For the manufacture of creams, emulsions, and gels, the color components are mixed with additional components which in the past have generally been used in these preparations. Such additional components are, for example, wetting agents or emulsifiers of the anionic or non-ionogenic type, like alkylbenzenesulfonates, fatty alcohol sulfates, alkyl sulfonates, fatty acid alkanol amides, and the addition products of ethylene oxide with fatty alcohols; thickeners (for example, methyl cellulose; starch; higher fatty alcohols; paraffin oil; and fatty acids); perfume oils, and hair conditioners like pantothenic acid and cholesterol. The above-mentioned additives are used in amounts customary for this purpose, such as wetting agents and emulsifiers in concentrations of 0.5%-30% by weight, and thickeners in concentrations of 0.1%-25% by weight, each based on the total weight of the preparation.

The hair coloring preparations according to the invention, regardless of whether they are a solution, emulsion, cream or gel, can be applied at an acid or neutral pH or at an alkaline pH, preferably in the range of 8-10, and at temperatures in the range from 15° C. to 40° C. Development of the dyeing properties of the composition takes place within about 30 minutes, after which the preparation is removed from the hair by rinsing. Then the hair is washed with a mild shampoo and dried.

The invention is further illustrated by the examples which follow. These examples are best embodiments, and are not to be construed in limitation thereof.

EXAMPLES 1–19

The 2,4-dichloro-3-aminophenol used as coupler component was prepared as the hydrochloride as follows.

85 g. of 2,4-dichloro-3-nitrophenol was reduced in 900 ml. of ethanol with 9 g. of Raney nickel as a catalyst at 40° C. and 20 excess atmosphere hydrogen pressure. After the reduction, the solution was liberated of the catalyst, acidified with hydrochloric acid, and prepared in the usual manner. 62 g. of 2,4-dichloro-3-aminophenol hydrochloride (equivalent to 70.4% of theory) was obtained in the form of white crystals with a decomposition point of 177°–183° C. The mass spectrum showed 178 mols (calc. 178). Analysis yielded the following values:

|  | % C | % H | % N | % Cl |
|---|---|---|---|---|
| Calculated | 33.57 | 2.80 | 6.53 | 49.65 |
| Found | 33.58 | 2.87 | 6.13 | 48.35 |

The 2,4,6-trichloro-3-aminophenol can be prepared in similar manner.

The hair colorants according to the invention were used in the form of a cream emulsion (i.e., an emulsion of cream viscosity), prepared as follows.

Into an emulsion of:

| Parts by Weight | Component |
|---|---|
| 10 | Fatty alcohols of $C_{12-18}$ chain length |
| 10 | Fatty alcohol sulfate (sodium salt $C_{12-18}$ chain length) |
| 75 | Water | were introduced 0.01 mol of the developer component listed in the following table and polyhalogen-substituted m-aminophenol. The emulsions were then adjusted to pH 9.5 by addition of ammonia, and the emulsions were made up with water to 100 parts by weight. The oxidative coupling was effected either with atmospheric oxygen or with 1% hydrogen peroxide solution as an oxidant, in the latter instance 10 parts by weight of hydrogen peroxide solution being added to 100 parts by weight of the emulsion. The resulting coloring creams, with or without additional oxidants, were applied to untreated 90% grey hair (human) and were left there for 30 minutes, during which time the composition developed its dyeing properties. The hair was washed with a commercial shampoo and was then dried. The colors obtained are shown in Table 1.

TABLE I

| Example | Developer | Coupler | With Air Oxidation | With 1% $H_2O_2$ Solution |
|---|---|---|---|---|
| 1 | p-Toluenediamine | 2,4-Dichloro-3-aminophenol | Dark brown | Black blue |
| 2 | p-Aminophenol | " | Brown-orange | Red-gold |
| 3 | 2,5-Diaminoanisole | " | Dark turquoise | Blue grey |
| 4 | p-Phenylenediamine | " | Brown grey | Violet grey |

TABLE I-continued

| Example | Developer | Coupler | With Air Oxidation | With 1% H$_2$O$_2$ Solution |
|---|---|---|---|---|
| 5 | 2,4,5,6-Tetraamino-pyrimidine | " | Blue | Black-blue |
| 6 | 2-Dimethylamino-4,5,6-triamino-pyrimidine | " | Light blue | Blue |
| 7 | 2-Morpholino-4,5,6-triaminopyrimidine | " | Grey-turquoise | Grey turquoise |
| 8 | 2-Methylamino-4,5,6-triaminopyrimidine | " | Blue grey | Dark blue |
| 9 | p-Toluenediamine | 4,6-Dichloro-3-aminophenol | Olive brown | Blue grey |
| 10 | 2,5-Diaminoanisole | " | Black blue | Black blue |
| 11 | 1-Phenyl-3-carbamoyl-4-aminopyrazolone | " | Violet | Violet |
| 12 | 2,4,5,6-Tetraaminopyrimidine | " | Violet | Dark violet |
| 13 | 2-Dimethylamino-4,5,6-triaminopyrimidine | " | Dark blue | Dark violet |
| 14 | 2-Methylamino-4,5,6-triaminopyrimidine | " | Dark violet | Dark violet |
| 15 | 2-Morpholino-4,5,6-triaminopyrimidine | " | Black blue | Dark blue |
| 16 | 2,6-bis-Dimethylamino-4,5-pyrimidine | " | Brown-orange | Light brown |
| 17 | p-Toluenediamine | 2,4,6-Trichloro-3-aminophenol | Brown grey | Brown grey |
| 18 | 2,5,Diaminoanisole | " | Olive grey | Olive grey |
| 19 | 1-Phenyl-3-carbamoyl-4-aminopyrazolone | " | Brown grey | Brown grey |

We claim:
1. An oxidizable developer-coupler combination for use in the dyeing of hair, comprising a water-soluble polyhalogen 3-aminophenol of the formula:

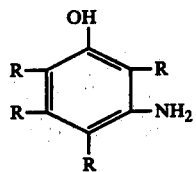

wherein two or three of the R's are halogen and the other R or R's are hydrogen, as the coupler, and a developer therefor.

2. The combination according to claim 1 wherein, in the coupler, the R's which designate halogen are selected from the group consisting of fluorine, chlorine and bromine.

3. The combination according to claim 1 wherein the coupler is 2,4-dichloro-3-aminophenol.

4. The combination according to claim 1 wherein the coupler is 4,6-dichloro-3-aminophenol.

5. The combination according to claim 1 wherein the developer is p-toluenediamine.

6. The combination according to claim 1 wherein the developer is p-aminophenol.

7. The combination according to claim 1 wherein the developer is 2.5-diaminoanisol.

8. The combination according to claim 1 wherein the developer is p-phenylenediamine.

9. The combination according to claim 1 wherein the developer is a tetraaminopyrimidine of the formula

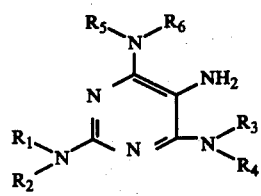

wherein $R_1$-$R_6$ represent hydrogen; $C_{1-4}$ alkyl; or —(CH$_2$)$_{1-4}$X, wherein X represents —OH, -halogen, —NH$_2$, —NHR' or —NR'R" wherein R' and R" represent $C_{1-4}$ alkyl; and where —NR'R" represents a 5 to 6 membered heterocyclic ring; and the R' and R" substituents together can be selected from the group consisting of tetramethylene, pentamethylene, azatetramethylene, azapentamethylene, oxatetramethylene, and oxapentamethylene.

10. The combination according to claim 9 wherein the developer is 2,4,5,6-tetraaminopyrimidine.

11. The composition according to claim 9 wherein the developer is 2-dimethylamino-4,5,6-triaminopyrimidine.

12. The composition according to claim 9 wherein the developer is 2-morpholino-4,5,6-triaminopyrimidine.

13. The composition according to claim 1 wherein the developer is 2-methylamino-4,5,6-triaminopyrimidine.

14. The composition according to claim 9 wherein at least one of the components of the composition are present in water-soluble salt form.

15. The composition according to claim 14 wherein the developer and coupler are in the form of their acetates.

16. The composition according to claim 1 wherein the developer and the coupler are present in about 1:1 molar equivalent ratio.

17. A preparation for use in the dyeing of hair, comprising a viscous aqueous carrier having a content of about 0.2% to 5% by weight of the developer-coupler combination according to claim 1.

18. The preparation according to claim 17 also containing an effective amount of hydrogen peroxide as oxidizer for the developer-coupler combination therein.

19. The preparation of claim 17 having a pH between 8 and 10.

20. A method of dyeing hair, which comprises applying to hair an effective amount of the preparation according to claim 17 and oxidizing the developer-coupler combination on said hair.

21. The method according to claim 20, wherein the developer-coupler combination is oxidized by air.

* * * * *